United States Patent
Ramdani et al.

(10) Patent No.: US 7,659,418 B2
(45) Date of Patent: Feb. 9, 2010

(54) METHOD OF PREPARING ORGANO DIALKYLALKOXYSILANE

(75) Inventors: Kamel Ramdani, Lyons (FR); Bernard Vogin, Chaponost (FR); Nathalie Guennount, Irigny (FR)

(73) Assignee: Rhodia Operations, Aubervilliers (FR)

( * ) Notice: Subject to any disclaimer, the term of this patent is extended or adjusted under 35 U.S.C. 154(b) by 39 days.

(21) Appl. No.: 10/518,685

(22) PCT Filed: Jun. 23, 2003

(86) PCT No.: PCT/FR03/01921

§ 371 (c)(1),
(2), (4) Date: Jun. 23, 2005

(87) PCT Pub. No.: WO04/000852

PCT Pub. Date: Dec. 31, 2003

(65) Prior Publication Data

US 2005/0245755 A1    Nov. 3, 2005

(30) Foreign Application Priority Data

Jun. 21, 2002 (FR) .................................. 02 07713
Dec. 2, 2002 (FR) .................................. 02 15114

(51) Int. Cl.
*C07F 7/04* (2006.01)

(52) U.S. Cl. ........................................ 556/445
(58) Field of Classification Search .................. 556/445
See application file for complete search history.

(56) References Cited

OTHER PUBLICATIONS

Urbaniak et al., {Synthesis and Reactivity in Inorganic and Metal-Organic Chemistry, Synthesis of Siloxyphosphines, 1988, 18 (7), 695-703}.*

* cited by examiner

*Primary Examiner*—Daniel M Sullivan
*Assistant Examiner*—Chukwuma O Nwaonicha
(74) *Attorney, Agent, or Firm*—Buchanan, Ingersoll & Rooney P.C.

(57) ABSTRACT

The invention relates to the preparation of organodialkylalkoxysilane using a continuous method consisting in bringing an alkanol into continuous contact with an omega-haloalkyl dialkylhalosilane in a countercurrent reactor, such as a plate column or a packed column. The reaction is performed in the aforementioned countercurrent reactor in the presence or absence of a non-reactive solvent with scavenging of the hydrochloric acid formed. The omega-haloalkyl dialkylalkoxysilane thus formed is particularly suitable for use as a starting material for the preparation of organosilicon compounds containing sulphur having general formula (I) by means of sulphidisation reaction on an alkaline metal polysulphide.

10 Claims, 1 Drawing Sheet

METHOD OF PREPARING ORGANO DIALKYLALKOXYSILANE

Figure 1:
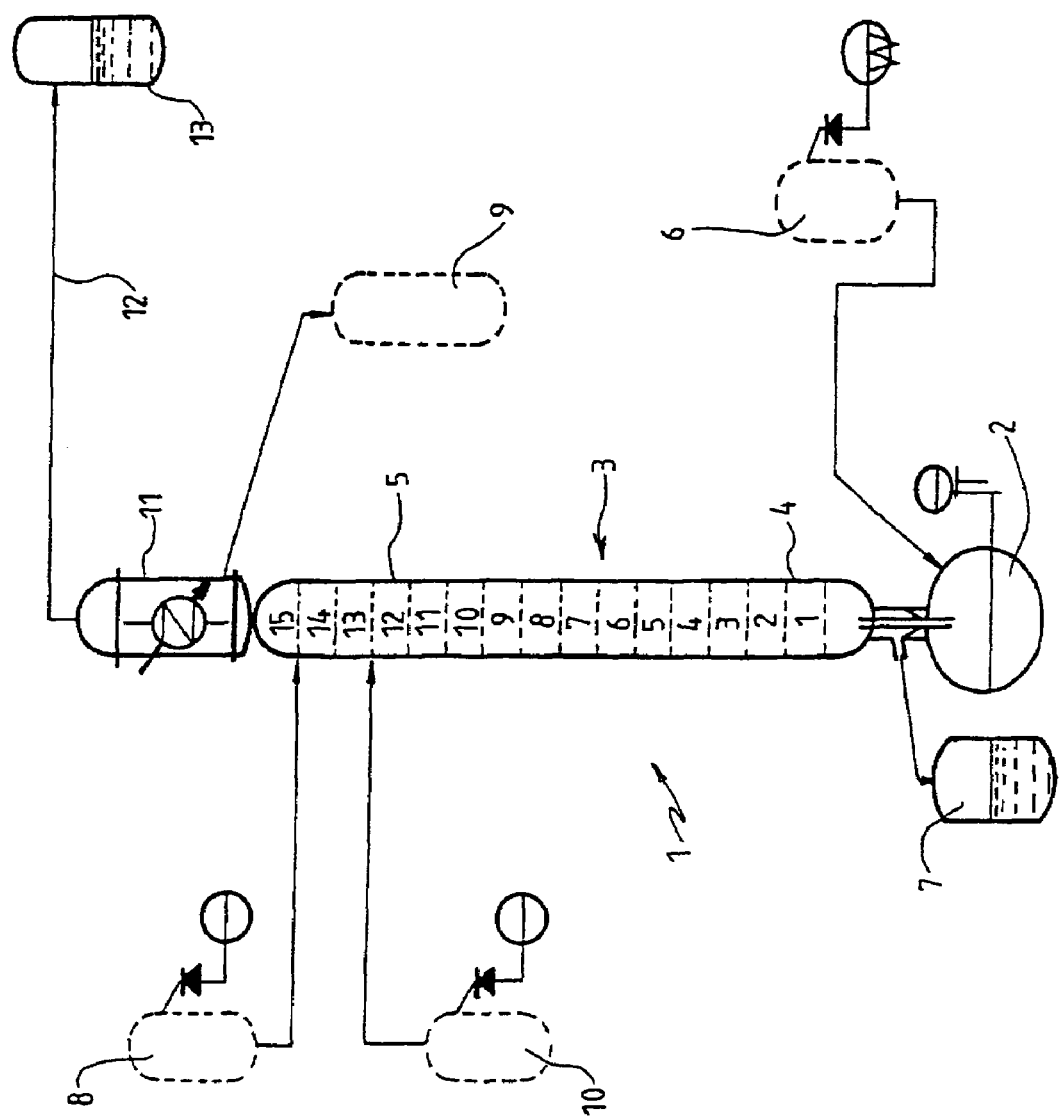

This application is an application under 35 U.S.C. Section 371 of International Application Number PCT/FR2003/001921 filed on Jun. 23, 2003.

The present invention relates to a process for preparing organo dialkylalkoxysilane by a continuous process in the presence of an alkanol on an omega-haloalkyl dialkylhalosilane.

The invention relates more particularly to the preparation of an ethoxypropylsilane from a chloropropylsilane. Known processes on this synthesis relate more specifically to dichloropropylsilane and trichloropropylsilane. The process according to the invention allows 3-chloropropyldimethylchlorosilane to be used as reactant, while giving ethoxydimethyl-3-chloropropylsilane with very high yields. The chemical reaction is as follows:

$$ClMe_2Si-CH_2CH_2CH_2Cl+EtOH \rightarrow (EtO)Me_2Si-CH_2CH_2CH_2Cl+HCl$$

The 3-chloropropyldimethylchlorosilane may be ethoxylated quantitatively and selectively in the presence of a base. The use, for example, of an organic base of tertiary amine type (including triethylamine) allows the acid formed to be neutralized stoichiometrically. However, the use of a base, and the lengthening and complication of the process that are associated with its use and its eventual removal, constitute a certain disadvantage. In the absence of base, moreover, the reaction leads to performance levels which are unsatisfactory under conditions conventionally used for this type of reaction: running ethanol into an initial charge of 3-chloro-propyldimethylchlorosilane. This is a batch reactor process which gives excellent results only if the raw material is dichloropropylmethylchlorosilane or trichloropropylchlorosilane: degree of conversion (DC)=100% and selectivity (RT)>95%. This is because the specificity of the dimethylchlorosilane moiety, compared for example with the trichlorosilane group, leads to a lower reactivity with respect to ethanol and, consequently, gives rise to more substantial formation of secondary products. These secondary products have come essentially from an oligomerization of the silane function, a reaction consecutive to the following reaction:

$$EtOH+HCl \rightarrow EtCl+H_2O$$

$$2[ClMe_2Si-CH_2CH_2CH_2Cl]+H_2O \rightarrow ClCH_2CH_2CH_2-SiMe_2-O-Me_2Si-CH_2CH_2CH_2Cl+HCl$$

The principal aim of the present invention is specifically to provide a high-performance process, of the type above, whose starting product is a monochlorotriorganosilane, especially 3-chloropropyldimethylchlorosilane, and which can be carried out in the absence of base.

This aim, among others, is achieved by the present invention, which relates in effect to a process for preparing organodialkylalkoxysilane by a continuous process which consists in contacting an alcohol, of alkanol type for example, continuously in countercurrent with an omega-haloalkyl-dialkylhalo-silane.

The conversions obtained are generally greater than 90% and may reach 100%, and the selectivities obtained are also very high.

The alcoholysis reaction deployed according to the invention may be represented schematically by the following equation:

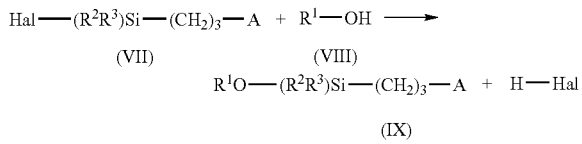

where:
the symbol Hal represents a halogen atom selected from chlorine, bromine and iodine atoms, the chlorine atom being preferred, the symbols $R^1$, which are identical or different, each represent a monovalent hydrocarbon group selected from a linear or branched alkyl radical having 1 to 15 carbon atoms and a linear or branched alkoxyalkyl radical having 2 to 8 carbon atoms;

the symbols $R^2$ and $R^3$, which are identical or different, each represent a monovalent hydrocarbon group selected from a linear or branched alkyl radical having 1 to 6 carbon atoms and a phenyl radical;

A represents a removable group selected alternatively from: a halogen atom Hal belonging to chlorine, bromine and iodine atoms, the chlorine atom being preferred; or a radical para-$R^0-C_6H_4-SO_2-O-$ where $R^0$ is a linear or branched C1-C4 alkyl radical, the tosylate radical para-$CH_3-C_6H_4-SO_2-O-$ being preferred; or a radical $R^0-SO_2-O-$ where $R^0$ is as defined above, the mesylate radical $CH_3-SO_2-O-$ being preferred; or a radical $R^0-CO-O-$ where $R^0$ is as defined above, the acetate radical $CH_3-CO-O-$ being preferred, the most preferred radical A being the chlorine atom.

According to the invention the continuous process therefore makes it possible to carry out, in a countercurrent reactor, both the alkoxylation reaction and the separation of the stream of alkanol of formula (VIII) and of H-Hal (generally HCl) from the stream of silanes. Subsequently it is possible, if desired, finally to separate the alkanol from the H-Hal. Thereafter the alcohol thus purified can be reinjected into the reactor. More specifically the procedure is such that within the reactor a descending liquid fluid comprising the silane of formula (VII) and an ascending gaseous fluid comprising the alcohol of formula (VIII) will circulate in countercurrent. Also present within the reactor, in the vapor state, is the product of formula H-Hal. Advantageously the inside of the reactor in which the alcoholysis reaction is carried out is composed of a packed column or a plate column so as to create reaction zones in liquid phase: the temperature is between the boiling temperature of the alcohol of formula (VIII) and the boiling temperature of the silane of formula (VII). The reaction is carried out in the reactor alternatively at atmospheric pressure or at reduced pressure or at superatmospheric pressure.

In the advantageous implementation of the invention the alcohol is introduced into the boiler and/or into the lower part of the column. The silane, for its part, is introduced at a location anywhere on the column above the zone where the alcohol is introduced. In this case the silane descends the column in countercurrent and reacts in countercurrent with the vaporized ethanol, which carries the HCl formed to a condenser situated at the top of the column, or else the mixture in the vapor state is separated elsewhere. The alkoxylated silane is recovered at the bottom of the column, in the boiler, and/or is taken off at the side in the lower part of the column.

The process comprises the stripping or vapor entrainment of the HCl formed from the reaction mixture and the shifting of the equilibrium by increasing the concentration of alkanol (ethanol) by distilling ethanol from the reaction mixture in order to remove HCl.

It is preferable, so as always to have an excess of alcohol, to operate the reactor by working with an alcohol/silane molar ratio of greater than 1 and, preferably, between 1.2 and 20. In the case of the ethanol/3-chloropropyldimethylchlorosilane pairing, this alcohol/silane molar ratio is greater than 1.2 and preferably greater than 3, and generally is at most 20.

It is preferable, moreover, in the advantageous implementation of the invention, to introduce the alcohol in the lower part of the column and the silane in the upper part of the column.

The column may be equipped in its internal structure with dumped or ordered packing or else with plates. Controlling the reflux rate is an advantageous means for adjusting the profile of temperatures in the column, but particularly for regulating the amount of H-Hal present in the column.

One operational improvement of this countercurrent reactor may consist in at least one side removal of the gaseous streams based on alcohol and on H-Hal at one or more locations of the column, in order to minimize the concentration of Hal in the reactor. It is known that H-Hal which is not removed can limit the shifting of the reaction at equilibrium and may give rise to parasitic reactions. A fresh alcohol stream or a stream resulting from recycling of the acidic alcohol may be injected into each removal zone in order to compensate the fluid removed.

As indicated above, in the case where the products corresponding to formulae (VII), (VIII) and (IX) have ethyl groups $R^1$ and methyl groups $R^2$ and $R^3$ and A and Hal represent a chlorine atom, the alcohol is an alcohol constituted by ethanol and the silane is 3-chloropropyldimethylchlorosilane, with formation of HCl.

If the reaction is conducted at atmospheric pressure the reaction temperature within the reactor, and in particular within the column, must be greater than that of the stripping carrier gas, i.e., for example, 78° C. in the case of ethanol, and less than the temperature of the 3-chloropropyldimethylchlorosilane, i.e., 178° C. It is therefore recommended to operate at reduced pressure in order to limit the solubility of HCl in the ethanol and to conduct the reaction at a temperature less than that corresponding to one atmospheric pressure, which allows the parasitic reactions to be limited and selectivity gains to be made.

The acidic alcohol, in other words the alcohol laden with HCl, must be purified before being recycled into the reaction mixture, by distillation, azeotropic distillation where appropriate, by adsorption on resin, by neutralization or by membrane separation.

The stripping of the HCl may be coupled with a stripping of the water present in the mixture, by operating at a temperature greater than the boiling temperature of water at the pressure in question.

The alcoholysis reaction in this countercurrent reactor may be carried out optionally in the presence of an organic solvent and/or an inert gas. The solvent is aprotic and relatively nonpolar, such as aliphatic and/or aromatic hydrocarbons. The solvent used has a boiling temperature at the service pressure (atmospheric pressure) of between the boiling temperature of the alcohol of formula (VIII), for example 77.8° C. for ethanol, and that of the silane of formula (VII), for example 178° C. for 3-chloropropyldimethylchlorosilane. As an appropriate solvent for the ethanol/3-chloropropyldimethylchlorosilane pairing mention may be made in particular of toluene, monochlorobenzene and xylene. The function of the solvent is to strip the hydrochloric acid (HCl) by mechanical entrainment (the alcohol is also entrained, and recycling after purification may be contemplated) and also to create a depletion zone (no HCl, or very little, at the bottom of the column) in order to minimize the parasitic chemical reactions.

The organodialkylalkoxysilane of formula (IX) thus obtained can be used more particularly as a starting product for preparing organosilicon compounds containing sulfur, of the general average formula (I):

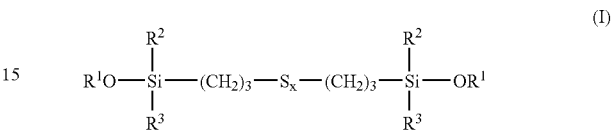

in which:

x is an integral or fractional number ranging from 1.5±0.1 to 5±0.1; and the symbols $R^1$, $R^2$, $R^3$, Hal and A are as defined above.

In the formula (I) above, the preferred radicals $R^1$ are selected from the following radicals: methyl, ethyl, n-propyl, isopropyl, n-butyl, $CH_3OCH_2$—, $CH_3OCH_2CH_2$— and $CH_3OCH(CH_3)CH_2$—; more preferably the radicals $R^1$ are selected from the following radicals: methyl, ethyl, n-propyl and isopropyl.

The preferred radicals $R^2$ and $R^3$ are selected from the following radicals: methyl, ethyl, n-propyl, isopropyl, n-butyl, n-hexyl and phenyl; more preferably the radicals $R^2$ and $R^3$ are methyls.

The integral or fractional number x ranges preferably from 3±0.1 to 5±0.1 and more preferably from 3.5±0.1 to 4.5±0.1.

The polysulfur monoorganoxysilanes corresponding to the formula (I) which are a specific objective of the present invention are those of formula:

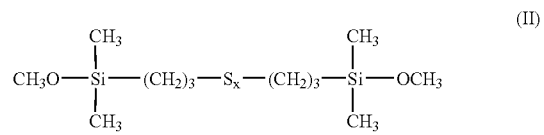

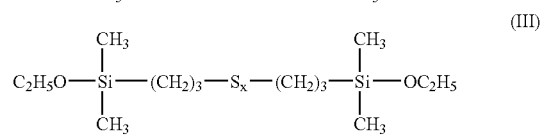

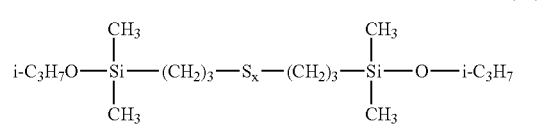

in which the symbol x is an integral or fractional number ranging from 1.5±0.1 to 5±0.1, preferably from 3±0.1 to 5±0.1 and more preferably from 3.5±0.1 to 4.5±0.1.

In the present specification it will be specified that the symbol x in the formulae (I), (II), (III) and (IV) is an integral fractional number representing the number of sulfur atoms present in one molecule of formula (I), (II), (III) and (IV).

In practice this number is the average of the number of sulfur atoms per molecule of compound under consideration, insofar as the selected synthesis route gives rise to a mixture of polysulfur products each having a different number of sulfur atoms. The polysulfur monoorganoxysilanes synthesized are in fact composed of a distribution of polysulfides, ranging from the monosulfide to heavier polysulfides (such as $S_{\geq 5}$, for example) centered on an average molar value (value of the symbol x) which is situated within the general ranges (x ranging from 1.5±0.1 to 5±0.1), preferentially (x ranging from 3±0.1 to 5±0.1) and more preferentially (x ranging from 3.5±0.1 to 4.5±0.1) mentioned above.

The products of formula (I) may be prepared as follows from the organodialkylalkoxysilane of formula (IX) prepared beforehand in the course of step b) by the continuous process of the invention, by reacting said product of formula (IX) in the course of step c) with an alkali metal polysulfide of formula (X) in accordance with the following reaction scheme: step c):

$$2[R^1O-(R^2R^3)Si-(CH_2)_3-A] + M_2S_x \longrightarrow$$
$$\text{(IX)} \quad \text{(X)}$$
$$\text{product of formula (1) + 2 M-A}$$

where:
the symbols $R^1$, $R^2$, $R^3$, A and x are as defined above,
the symbol M represents an alkali metal,
the reaction is carried out:
by reacting, at a temperature ranging from 20° C. to 120° C., either the reaction mixture obtained at the end of step (b), or the monoorganoxydiorganosilyl-propyl derivative of formula (IX), taken in isolation after separation from said reaction mixture, with the metal polysulfide of formula (X) in the anhydrous state, using 0.5±15 mol % of metal polysulfide of formula (X) per mole of the reactant of formula (IX) and optionally operating in the presence of an inert polar (or nonpolar) organic solvent,
and by isolating the bis(monoorganoxysilylpropyl) polysulfide of formula (I) that is formed.

The continuous process according to the present invention allows access to bis(monoorganoxysilylpropyl) polysulfides of formula (I). The diorganohalosilanes of formula (VII) can be prepared advantageously on the industrial scale by a process such as, in particular, that described in WO-A-99/31111, cited as reference.

The process according to the invention for preparing products of formula (I) proceeds virtually quantitatively, without employing reactants and/or without forming secondary products which are toxic compounds or pollutants to the environment (such as $H_2S$ and alkali metals in the case of the polysulfiding step).

The starting product in step b) of formula (VII) can be prepared according to the following process: step a)

$$\text{Hal}-\underset{\underset{R^3}{|}}{\overset{\overset{R^2}{|}}{Si}}-H + CH_2=CH-CH_2-A \longrightarrow$$
$$\text{(V)} \qquad \text{(VI)}$$

-continued
$$\text{Hal}-\underset{\underset{R^3}{|}}{\overset{\overset{R^2}{|}}{Si}}-(CH_2)_3-A$$
$$\text{(VII)}$$

where:
the symbol Hal represents a halogen atom selected from chlorine, bromine and iodine atoms, the chlorine atom being preferred, and
the symbols A, $R^2$ and $R^3$ are as defined above,
the reaction being carried out:
by reacting, at a temperature ranging from −10° C. to 200° C., one mole of the diorganohalosilane of formula (V) with a molar amount which is stoichiometric or different from the stoichiometry of the allyl derivative of formula (VI), the operation being carried out in a homogeneous or heterogeneous medium in the presence of an initiator consisting:
either of a catalytic activator consisting of:
(i) at least one catalyst comprising at least one transition metal or one derivative of said metal, taken from the group consisting of Co, Ru, Rh, Pd, Ir and Pt; and optionally (2i) at least one hydrosilylation reaction promoter,
or of a photochemical activator, consisting in particular of appropriate ultraviolet radiation or appropriate ionizing radiation,
and optionally by isolating the diorganohalosilylpropyl derivative of formula (VII) that is formed.

According to one particularly suitable embodiment of the invention the process which has just been described consists in linking together steps (a), (b) and (c) in the definition of which the products of formulae (I), (V), (VI), (VII), (VIII) and (IX) have ethyl groups $R^1$ and methyl groups $R^2$ and $R^3$ and the removable group A corresponds to the symbol Hal representing a halogen atom selected from chlorine, bromine and iodine atoms, and, preferably, a chlorine atom.

Step (a) consists in reacting the diorganohalosilane of formula (V) with the allyl derivative of formula (VI) in the presence of a selected initiator. The initiator used embraces all of the initiators, corresponding to the types indicated above, which are effective in activating the reaction between a ≡SiH function and an ethylenic unsaturation.

According to one preferred arrangement concerning the initiator, the latter is selected from catalytic activators. These catalytic activators comprise:
as the catalyst (or catalysts), (i): (i-1) at least one finely divided elemental transition metal; and/or (i-2) a colloid of at least one transition metal; and/or (i-3) an oxide of at least one transition metal; and/or (i-4) a salt derived from at least one transition metal and a mineral or carboxylic acid; and/or (i-5) a complex of at least one transition metal equipped with organic ligand(s) which may possess one or more heteroatoms and/or organosilicon ligands; and/or (i-6) a salt as defined above in which the metal moiety is equipped with ligand(s) as also defined above; and/or (i-7) a metal species selected from the aforementioned species (elemental transition metal, oxide, salt, complex, complexed salt) where the transition metal is combined this time with at least one other metal selected from the class of the elements of groups 1b, 2b, 3a, 3b, 4a, 4b, 5a, 5b, 6b, 7b and 8 (with the exception of Co, Ru, Rh, Pd, Ir and Pt) of the Periodic Table as published in "Chemistry and Physics, 65th edition, 1984-1985, CRC Press, Inc.", said other metal being taken in its elemental form or in a molecular form, it being possible for said combination to give rise to a bimetallic or polymetallic species; and/or (i-8) a metal species selected from the aforementioned species (elemental transition metal and transition metal/other metal combination; oxide, salt, complex and complexed salt on a transition metal base or on a transition metal/other metal combination base which is supported on an inert solid support such as alumina, silica, carbon black, a clay, titanium oxide, an aluminosilicate, a mixture of aluminum and zirconium oxides, or a polymer resin;

as the optional promoter (or promoters) (2i): a compound, which may take for example the form of a ligand or of an ionic compound, taken in particular from the group consisting of: an organic peroxide; a carboxylic acid; a carboxylic salt; a tertiary phosphine; an amine; an amide; a linear or cyclic ketone; a trialkylhydrosilane; benzothiazole; phenothiazine; a trivalent metal —$(C_6H_5)_3$ compound where metal=As, Sb or P; a mixture of amine or of cyclohexanone with an organosilicon compound containing one or more —Si≡H groups; the compounds $CH_2$=CH—$CH_2$—OH or $CH_2$=CH—$CH_2$—$OCOCH_3$; a lactone; a mixture of cyclohexanone with triphenylphosphine; an ionic compound such as for example a nitrate or a borate of an alkali metal or of imidazolinium, a phosphonium halide, a quaternary ammonium halide or a tin(II) halide.

According to one more preferred arrangement concerning the initiator, the latter is selected from the preferred catalytic activators mentioned above which comprise, as the catalyst (or catalysts) (i), one and/or other of the metallic species (i-1) to (i-8) where the transition metal belongs to the following subgroup: Ir and Pt.

According to one even more preferred arrangement concerning the initiator, the latter is selected from the preferred catalytic activators mentioned above which comprise, as the catalyst (or catalysts) (i), one and/or other of the metallic species (i-1) to (i-8) where the transition metal is Ir. In the context of this even more preferred arrangement, suitable Ir-based catalysts are especially:

[IrCl(CO) $(PPh_3)_2$]
[Ir (CO)H$(PPh_3)_3$]
[Ir$(C_8H_{12})$ $(C_5H_5N)P(C_6H_{11})_3$]$PF_6$
[$IrCl_3$],n$H_2O$
$H_2$[$IrCl_6$],n$H_2O$
$(NH_4)_2IrCl_6$
$Na_2IrCl6$
$K_2IrCl_6$
$KIr(NO)Cl_5$
[Ir $(C_8H_{12})_2$]$^+BF_4^-$
[IrCl $(CO)_3$]$_n$
$H_2IrCl_6$
$Ir_4(CO)_{12}$
$Ir(CO)_2(CH_3COCHCOCH_3)$
$Ir(CH_3COCHCOCH_3)$
$IrBr_3$
$IrCl_3$
$IrCl_4$
$IrO_2$
$(C_6H_7)$ $(C_8H_{12})$ Ir.

In the context of the even more preferred arrangement mentioned above, other Ir-based catalysts which are even more suitable are taken from the group of the iridium complexes of formula:

[Ir($R^4$)Hal]$_2$ (XI)

where:
the symbol $R^4$ represents a conjugated or nonconjugated, linear or cyclic (mono- or polycyclic) polyene ligand having 4 to 22 carbon atoms and from 2 to 4 ethylenic double bonds;
the symbol Hal is as defined above.

As an example of iridium complexes of formula (XII) which are even more suitable mention will be made of those in whose formula:
the symbol $R^4$ is selected from 1,3-butadiene, 1,3-hexadiene, 1,3-cyclohexadiene, 1,3-cyclooctadiene, 1,5-cyclooctadiene, 1,5,9-cyclododecatriene and norbornadiene and
the symbol Hal represents a chlorine atom.

As specific examples of iridium complexes which are even more suitable mention will be made of the following catalysts:
di-μ-chlorobis(η-1,5-hexadiene)diiridium,
di-μ-bromobis(η-1,5-hexadiene)diiridium,
di-μ-iodobis(η-1,5-hexadiene)diiridium,
di-μ-chlorobis(η-1,5-cyclooctadiene)diiridium,
di-μ-bromobis(η-1,5-cyclooctadiene)diiridium,
di-μ-iodobis(η-1,5-cyclooctadiene)diiridium,
di-μ-chlorobis(η-2,5-norbornadiene)diiridium,
di-μ-bromobis(η-2,5-norbornadiene)diiridium,
di-μ-iodobis(η-2,5-norbornadiene)diiridium.

The catalyst may be used—and this is another preferential arrangement—in a homogeneous medium, as described in JP-B-2 938 731. In this context the reaction may be conducted continuously, semicontinuously or batchwise. At the end of operation the product of the reaction is separated and collected by distillation of the reaction mixture, and the catalyst can be recycled by producing a new charge of reactants on a distillation residue containing the catalyst from the distillation step of the product of the preceding operation, with complementary addition of new catalyst where appropriate. Where complexes are employed the recycling of the catalyst can be enhanced by further adding a small amount of ligand.

The catalyst may also be used in heterogeneous medium. This operating method has recourse in particular to the employment of a catalyst which is supported on an inert solid support of the type of those defined above. This operating method makes it possible to carry out the reaction in a fixed-bed reactor operating continuously, semicontinuously or batchwise with recycling. It is also possible to carry out the reaction in a standard stirred reactor operating continuously, semicontinuously or batchwise.

As far as the other reaction conditions are concerned, the reaction is carried out within a wide range of temperatures, ranging preferably from −10° C. to 100° C., under atmospheric pressure or under a pressure greater than atmospheric pressure, which may reach or even exceed 20×10$^5$ Pa.

The amount of the allyl derivative of formula (VI) used is preferably from 1 to 2 mol per mole of organosilicon compound. As for the amount of catalyst(s) (i), expressed by weight of transition metal taken from the group consisting of Co, Ru, Rh, Pd, Ir and Pt, it is situated within the interval ranging from 1 to 10 000 ppm, preferably ranging from 10 to 2000 ppm and more preferably ranging from 50 to 1000 ppm, these figures being based on the weight of organosilicon compound of formula (V) or (IX). The amount of promoter(s) (2i), when one or more promoters are used, expressed in numbers of moles of promoter(s) per gram-atom of transition metal taken from the group consisting of Co, Ru, Rh, Pd, Ir and Pt, is situated in the interval ranging from 0.1 to 1000, preferably ranging from 0.5 to 500 and more preferably ranging from 1 to 300. The diorganohalosilylpropyl derivative of formula (VII) is obtained with a molar yield of at least 80%, based on the starting organosilicon compound of formula (V).

According to one preferred arrangement the anhydrous metal polysulfides of formula (X) are prepared by reacting an alkali metal sulfide, optionally containing water of crystallization, of formula $M_2S$ (XII), in which the symbol M has the meaning given above (alkali metal), with elemental sulfur, operating at a temperature ranging from 60° C. to 300° C., optionally under pressure and also optionally in the presence of an anhydrous organic solvent.

Advantageously the alkali metal sulfide $M_2S$ employed is the industrially available compound, which is generally in the form of a sulfide hydrate: one alkali metal sulfide of this type which is highly suitable is the $Na_2S$ sulfide available commercially, which is a hydrated sulfide containing 55 to 65% by weight of $Na_2S$.

According to a more preferred arrangement for conducting step (c) the anhydrous metal polysulfides of formula (X) are prepared beforehand from an alkali metal sulfide $M_2S$ in the form of a hydrated sulfide, according to a procedure which consists in linking together the following operating phases (1) and (2):

phase (1), where the alkali metal sulfide hydrate is dehydrated by applying the appropriate method which makes it possible to remove the water of crystallization while retaining the alkali metal sulfide in the solid state throughout the dehydration phase;

phase (2), where subsequently one mole of dehydrated alkali metal sulfide obtained is contacted with n(x-1) moles of elemental sulfur, the operation being carried out at a temperature ranging from 20° C. to 120° C., optionally under pressure and optionally again in the presence of an anhydrous organic solvent, the aforementioned factor n being situated within the range from 0.8 to 1.2 and the symbol x being as defined above.

With regard to phase (1), as a highly suitable dehydration protocol mention will be made in particular of the drying of the hydrated alkali metal sulfide, operating under a partial vacuum ranging from $1.33 \times 10^2$ Pa to $40 \times 10^2$ Pa and bringing the compound to be dried to a temperature ranging, at the beginning of drying, from 70° C. to 85° C., then by gradually raising the temperature in the course of drying from the zone ranging from 70° C. to 85° C. until it reaches the zone ranging from 125° C. to 135° C., in accordance with a program which envisages a first temperature rise of +10° C. to +15° C. after a first period varying from 1 hour to 6 hours, followed by a second temperature rise of +20° C. to +50° C. after a second period varying from 1 hour to 4 hours.

With regard to phase (2), as a highly suitable sulfiding protocol mention will be made of the implementation of this reaction in the presence of an anhydrous organic solvent; appropriate solvents are, in particular, lower (C1-C4) aliphatic alcohols which are anhydrous, such as anhydrous methanol or ethanol, for example. The number of atoms of elemental sulfur $S_x$ in the metal polysulfide $M_2S_x$ is a function of the molar ratio of S with respect to $M_2S$; for example, the use of 3 mol of S (n=1 and x−1=3) per mole of $M_2S$ gives the alkali metal tetrasulfide of formula (X) where x=4.

To return from this to the implementation of step (c), this latter step is carried out in a wide range of temperatures, ranging preferably from 50° C. to 90° C., operating more preferably in the presence of an organic solvent and, in that context, making use advantageously of the alcohols referred to above with regard to the conduct of phase (2).

The product M-A, and in particular the halide M-Hal, formed in the course of reaction is generally removed at the end of the step by means for example of filtration.

The bis(monoorganoxydiorganosilylpropyl) polysulfide of formula (I) that is formed is obtained with a molar yield of at least 80%, based on the starting monoorganoxydiorganosilylpropyl derivative of formula (IX).

The examples which follow illustrate the present invention without limiting its scope; reference will be made to the attached drawing, in which the single FIGURE represents diagrammatically the reaction apparatus including a column which is used in said examples.

In the single FIGURE it can be seen that the apparatus 1 comprises at its base a boiler 2 and a column 3 with a diameter of 40 mm, comprising a lower part 4 including the foot of the column and an upper part 5 including the head of the column. The column contains 15 plates labeled 1 to 15. The plates are made of perforated glass. The column 3 is equipped with an ethanol feed tank 6, which feeds the boiler 2 and certain plates of the bottom part 4 of the column, and also with a liquid recovery tank 7. The column 3 is equipped with a second feed tank 8 for optional feeding with liquid ethanol, which allows some of the plates in the upper part 5 of the column 3 to be fed, in order to simulate a purified ethanol reflux. The column 3 has an ethanol recovery tank 9 which constitutes the distillate and a starting silane feed tank 10. The silane is introduced onto a plate in the upper part 5 of the column, and the ethanol in the lower part. The upper part 5 of the column is surmounted by a condenser 11 connected via the pipeline 12 to the HCl suppression column 13 (HCl trap).

EXAMPLE 1

This example describes the preparation of bis(monoethoxydimethylsilylpropyl) tetrasulfide of formula (III) in which the number x is centered on 4. The reaction scheme concerned by this example is the following one:

Step (a):

$(CH_3)_2HSiCl$ + $CH_2$=$CH$—$CH_2$—$Cl$ ⟶
     1                    2

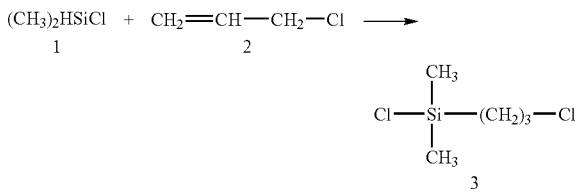

Step (b):

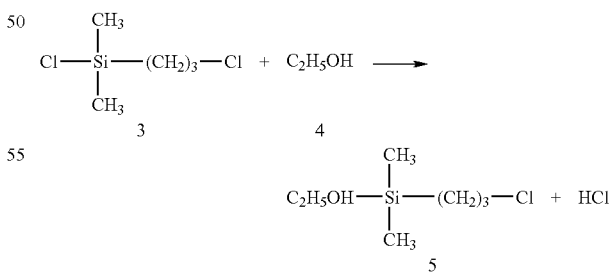

Step (c):

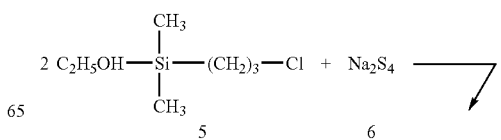

-continued

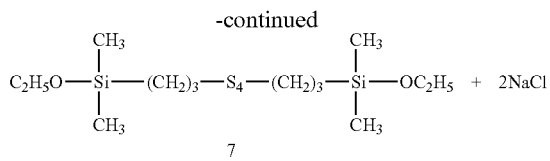

in which the reactant 6 is obtained according to the following equation:

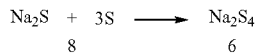

1) Step (a): Synthesis of 3:

A 1 liter stirred glass reactor equipped with a jacket and a stirrer and surmounted by a distillation column is charged with 165 g of allyl chloride 2 with a purity of 97.5% by weight (2.10 mol) and 0.229 g of catalyst [Ir(COD)Cl]$_2$ where COD=1,5-cyclooctadiene and the mixture is stirred in order to dissolve the catalyst completely. The temperature of the mixture is adjusted to 20° C. using the heat-exchange fluid circulating in the jacket.

Dimethylhydrochlorosilane 1, with a purity of 99% by weight, is introduced into the reaction mixture via a dip tube, using a pump: 196.5 g (2.06 mol) of 1 are introduced over 2 hours 35 minutes. The flow rate of introduction is adjusted in order to maintain the temperature of the reaction mixture at between 20 and 25° C., taking into account the strongly exothermic nature of the reaction. The reaction mixture is kept with stirring for 20 minutes after the end of the introduction of the dimethylhydrochlorosilane 1.

At the end of the stirring time a sample is taken for analysis. The results are as follows: degree of conversion of the dimethylhydrochlorosilane 1=99.8%, and selectivity for chloropropyldimethylchlorosilane 3=92.7% (by analysis by gas chromatography).

The reaction mixture is subsequently distilled under vacuum (approximately 35×10$^2$ Pa) at approximately 40° C. to give two main fractions: ∈ the light products (residual allyl chloride 2 and residual traces of dimethylhydrochlorosilane 1, accompanied essentially by chloropropyldimethylchlorosilane 3; ∉ chloropropyldimethylchlorosilane 3, with a molar purity of more than 98%. A distillation residue consisting of heavier products, and catalyst, then remains. Molar yield: 85%.

2) Step (b): Synthesis of 5:

As indicated above, a column as shown in the single FIGURE is used.

Chloropropyldimethylchlorosilane, stored in the feed tank 10, and ethanol, stored in the feed tanks 1 and 3, are injected directly into column 1, at plates 13 and 3 respectively. The column 1 is charged with an appropriate inert solvent, in the present case toluene. The function of the solvent is to strip the hydrochloric acid (HCl) by mechanical entrainment, the ethanol also being entrained and optionally recycled after purification. The solvent also creates a depletion zone (no HCl or very little in the lower part of the column), thereby making it possible to restrict the incidence of parasitic chemical reactions.

Toluene is brought to boiling in the boiler (2) by means of electrical resistors. This startup phase takes place with total reflux of the column in order to charge the plates of the column. Thereafter the reflux rate is regulated by a valve situated between the condenser (6) and the distillate recovery tank (4) but not shown in the single FIGURE.

The ethanol is injected into the column in liquid or vapor phase at plate 3 of the lower part 4 of the column. The ethanol flow rate is 100 g/h. The chloropropyldimethylchlorosilane is injected at plate 13 in liquid phase, with a flow rate of 120 g/h. The EtOH: silane molar ratio is 3.17.

The ethanol vaporizes in the column and, during its ascension, meets the chloropropyldimethylchlorosilane in liquid phase which is descending toward the boiler. The experiment lasts for 5 hours and the overall degree of conversion of chloropropyldimethylchlorosilane to chloropropyldimethylethoxysilane is from 92% to 94% with a selectivity of more than 90%.

3) Step (c): Synthesis of 7:

3.1) Preparation of Anhydrous Na$_2$S$_4$ 6:

Phase 1: drying of Na$_2$S hydrate:

43.6 g of industrial Na$_2$S hydrate flakes containing approximately 60.5% by weight of Na$_2$S are introduced into the 1-liter round-bottomed glass flask of a rotary evaporator. The flask is placed under an argon atmosphere and then under reduced pressure at 13.3×10$^2$ Pa.

The flask is immersed in an oil bath, whose temperature is then brought to 76° C. This temperature is maintained for 2 hours. Subsequently a protocol for increasing the temperature of the oil bath is applied in order to avoid melting the Na$_2$S, which occurs between 85 and 90° C. approximately. The purpose of the gradual increase in temperature is to accompany the change in the melting temperature of the product to be dried, which increases when the product undergoes dehydration. The protocol applied is as follows: 1 hour at 82° C., 2 hours at 85° C., 1 hour at 95° C., 1 hour at 115° C. and finally 1 hour at 130° C. It should be noted that this protocol can be odified according to the amount to be dried, the operating pressure and other parameters effecting the rate at which the water is removed. The amount of water removed, measured by mass difference, is 17.2 g, corresponding to a moisture content of 39.5% by weight.

Phase 2: synthesis of Na$_2$S$_4$ 6:

The Na$_2$S (26 g) dried according to the protocol described above is placed in suspension in 400 ml of anhydrous ethanol and transferred by suction into a stirred, jacketed, one-liter glass reactor equipped with a condenser with a possibility for reflux. 31.9 g of sulfur and also 200 ml of anhydrous ethanol are additionally introduced into this reactor. The temperature of the mixture is brought to approximately 80° C. (slight boiling of the ethanol) and the mixture is stirred at 600 rpm. The mixture is held at 80° C. for 2 hours. Gradually the solids (Na$_2$S and sulfur) disappear and the mixture changes from yellow to orange, then to brown. At the end of reaction the mixture is homogeneous at 80° C.; this gives approximately 58 g of anhydrous Na$_2$S$_4$ (0.33 mol) in 600 ml of ethanol.

3.2) Preparation of 7:

114 g of chloropropyldimethylethoxysilane 5 with a molar purity of 96.6% (i.e., 0.61 mol) are introduced via a dip tube, using a pump, into the anhydrous Na$_2$S$_4$ in 600 ml of ethanol, prepared above, which is maintained in its preparation reactor at 80° C. (slight boiling of the ethanol) and stirred at 600 rpm. A sodium chloride precipitate appears. When the introduction of chloropropyldimethylethoxysilane 5 is at an end, the mixture is held at 80° C. for 2 hours. Subsequently the mixture is cooled to room temperature, withdrawn and then filtered to remove the suspended solids, including the sodium chloride. The filtercake is washed with ethanol in order to extract as much as possible of the organic products from it. The filtrate is reintroduced into the reactor in order to be distilled therein under reduced pressure (approximately 20×10² Pa) for the purpose of removing the ethanol and any light products. 114 g of residue are recovered, which corresponds to bis(monoethoxydimethylsilylpropyl) tetrasulfide, assayed at a purity of 97% (molar).

This gives a mass yield of bis(monoethoxydimethylsilylpropyl) tetrasulfide of 87%.

Checking by $^1$H NMR, by $^{29}$Si NMR and $^{13}$C NMR makes it possible to verify that the structure obtained is in accordance with the formula (III) given in the description.

The average number of S atoms per molecule of formula (III) is 3.9±0.1 (x=3.9±0.1).

EXAMPLES 2 to 8

Step b) of example 1 is carried out again with the exception that the sites at which the alcohol is injected into the column, and/or the EtOH/silane molar ratio, and/or the reflux rate are modified. The results obtained are collated in Table 1 below, where DC and RT represent respectively the degree of conversion of chloropropyldimethylchlorosilane and the selectivity for chloropropyldimethylethoxysilane:

TABLE 1

| Example | Plate of EtOH injection | Plate of silane injection | EtOH/silane molar ratio | DC | RT | Reflux rate |
| --- | --- | --- | --- | --- | --- | --- |
| 1 | 12 | 13 | 1.2 | 20 | 88 | 0.5 |
| 2 | 12 | 13 | 3 | 70 | 93 | 0.5 |
| 3 | 12 | 13 | 6 | 68 | 91 | 0.5 |
| 4 | 3 | 13 | 1.2 | 35 | 89 | 0.5 |
| 5 | 3 | 13 | 3 | 92 | 91 | 0.5 |
| 6 | 3 | 13 | 6 | 91 | 91 | 0.5 |
| 7 | 3 | 13 | 10 | 89 | 90 | 0.5 |
| 8 | 3 | 13 | 3 | 93.5 | 86 | 1 |

From table 1 it emerges that it is preferable to have an EtOH/silane molar ratio of more than 3 in order to ensure that DC and RT values of more than 90 are obtained.

It is also apparent that it is preferable to inject EtOH onto plate 3 rather than onto plate 12. In this latter case the reaction volume is inadequate.

Another parameter is the reflux rate. This reflux rate controls the temperature level in the column but in particular in the amount of HCl (dissolved in the ethanol). And it is this acid which activates parasitic chemical reactions: example 8 is carried out with a reflux twice as great as in example 5, and, with all other things being equal, leads to a slight increase in the yield but to the detriment of the selectivity (86% and 91% respectively for examples 8 and 5).

EXAMPLE 9

A continuous reaction is carried out in the same column as for the preceding examples but without inert solvent. On this occasion the boiler (2) is charged with ethanol (1200 ml). The column (1) is charged by bringing the ethanol in the boiler (2) to boiling and by working at total reflux. When the steady-state regime has been attained the reflux is regulated and the 3-chloropropyldimethylchlorosilane is injected onto plate 13.

The ethanol flow rate (gas phase) is controlled by keeping the level in the boiler constant. The ethanol flow rate is 500 g/h and the chloropropyldimethylchlorosilane flow rate is 150 g/h, giving an EtOH:silane molar ratio of 12. The yield of the reaction is 100% irrespective of the reflux rate. Conversely the selectivity is a function of this reflux rate: from 50% for a reflux of 750 g/h to more than 85% for a zero reflux. It should be noted that in the column used, even at zero reflex, a fraction of the ethanol is condensed directly in the column. This can be avoided by introducing chloropropyldimethylchlorosilane preheated to 80° C. beforehand in order to prevent the cooling of the ethanol and its condensation.

EXAMPLE 10

Same experiment as example 3 with introduction of the chloropropyldimethylchlorosilane at plate 7. The results are identical to the preceding example: DC 100% and RT>85%.

The invention claimed is:

1. A continuous process for preparing an organodialkylalkoxysilane of formula (IX):

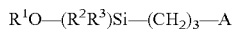

Comprising the steps of:
a) continuously contacting an alcohol of formula (VIII): R$^1$—OH in countercurrent with a silane of formula (VII): Hal-(R$^2$R$^3$)Si—(CH$_2$)$_3$—A, in order to carry out the alcoholysis reaction of said silane in order to obtain the silane of formula (IX) and a product of formula H-Hal, the operation being carried out with stripping of the product of formula H-Hal formed, and
b) recovering the organodialkylalkoxysilane formed in the reactor, in which formulae the symbol Hal represents a halogen atom selected from chlorine, bromine and iodine atoms, the chlorine atom being preferred;
the symbols R$^1$, which are identical or different, each represent a monovalent hydrocarbon group selected from a linear or branched alkyl radical having 1 to 15 carbon atoms and a linear or branched alkoxyalkyl radical having 2 to 8 carbon atoms; the symbols R$^2$ and R$^3$, which are identical or different, each represent a monovalent hydrocarbon group selected from a linear or branched alkyl radical having 1 to 6 carbon atoms and a phenyl radical; and
A represents a removable group selected alternatively from: a halogen atom Hal belonging to chlorine, bromine and iodine atoms, or a radical para-R$^0$—C$_6$R$_4$—SO$_2$—O— wherein R$^0$ is a linear or branched C1-C4 alkyl radical, or a radical R$^0$—SO$_2$—O— wherein R$^0$ is as defined above, or a radical R$^0$—CO—O— wherein R$^0$ is as defined above.

2. The process according to claim 1, wherein within the reactor a descending liquid fluid comprising the silane of formula (VII) and an ascending gaseous fluid comprising the alcohol of formula (VIII) will circulate in countercurrent.

3. The process according to claim 1, wherein the alcoholysis reaction is carried out within the reactor at a temperature between the boiling temperature of the alkanol of formula (VIII) and the boiling temperature of the starting silane of formula (VII), the reaction being carried out in the reactor alternatively at atmospheric pressure or at reduced pressure or at superatmospheric pressure.

4. The process according to claim 1, wherein the silane of formula (VII) is 3-chloropropyldimethylchlorosilane, Hal and A are chlorine and the alcohol of formula (VIII) is ethanol.

5. The process according to claim 4, wherein the 3-chloropropyldimethylchlorosilane, is introduced in the upper part of the reactor, the ethanol in the lower part, the reaction temperature in the column is greater than 77.80° C. and less than 178° C. at atmospheric pressure and the hydrochloric acid formed is stripped by the ethanol.

6. The process according to claim 1, wherein the reaction is carried out in the presence of an organic solvent or an inert gas, said solvent having a boiling temperature at the operating pressure which is between the boiling temperature of the ethanol of formula (VIII) and that of the silane of the formula (VII).

7. The process according to claim 6, wherein the solvent is toluene, monochlorobenzene or xylene and the products corresponding to formulae (I) to (XI) have ethyl groups $R^1$ and methyl groups $R^2$ and $R^3$ and A and Hal represent a chlorine atom.

8. The process according to claim 1, wherein the pressure inside the reactor is less than atmospheric pressure, atmospheric pressure or greater than atmospheric pressure.

9. The process according to claim 1, wherein the alcohol/silane molar ratio is greater than 1.

10. The process according to claim 1, wherein the countercurrent reactor consists of a column equipped in its internal structure with a dumped or ordered packing or with plates.

* * * * *